United States Patent
Chen et al.

(10) Patent No.: US 9,446,998 B2
(45) Date of Patent: Sep. 20, 2016

(54) PARAFFINIC JET AND DIESEL FUELS AND BASE OILS FROM VEGETABLE OILS VIA A COMBINATION OF HYDROTREATING, PARAFFIN DISPROPORTIONATION AND HYDROISOMERIZATION

(71) Applicants: Cong-Yan Chen, Kensington, CA (US); Dennis John O'Rear, Petaluma, CA (US); Thomas Francis Finger, Walnut Creek, CA (US); Stephen Joseph Miller, San Francisco, CA (US); Alexander Kuperman, Orinda, CA (US)

(72) Inventors: Cong-Yan Chen, Kensington, CA (US); Dennis John O'Rear, Petaluma, CA (US); Thomas Francis Finger, Walnut Creek, CA (US); Stephen Joseph Miller, San Francisco, CA (US); Alexander Kuperman, Orinda, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 14/729,831

(22) Filed: Jun. 3, 2015

(65) Prior Publication Data
US 2015/0266796 A1  Sep. 24, 2015

Related U.S. Application Data

(63) Continuation of application No. 13/841,226, filed on Mar. 15, 2013, now abandoned.

(60) Provisional application No. 61/754,375, filed on Jan. 18, 2013.

(51) Int. Cl.
*C07C 6/00*  (2006.01)
*C07C 6/02*  (2006.01)
(Continued)

(52) U.S. Cl.
CPC ............. *C07C 6/04* (2013.01); *B01J 23/6527* (2013.01);
(Continued)

(58) Field of Classification Search
CPC ............ C10G 3/42; C10G 2300/1018; C10G 2400/10; C10G 2300/1014; C10G 3/47; C10G 2400/02; C10G 2400/08; C10G 3/50; C10G 2400/04; C10G 3/44; C10G 2300/1011; C07C 2521/04; C07C 1/26; C07C 1/0485; C07C 2521/08; C07C 2523/75
USPC ................................................. 585/254, 310
See application file for complete search history.

(56) References Cited

U.S. PATENT DOCUMENTS 3,657,109 A    4/1972  Beyaert
3,699,035 A    10/1972 Hughes et al.
(Continued)

FOREIGN PATENT DOCUMENTS

WO    0116059 A1   3/2001

OTHER PUBLICATIONS

R. L. Burnett et al., "Mechanism and Poisoning of the Molecular Redistribution Reaction of Alkanes with a Dual-Functional Catalyst System", Journal of Catalysis, 1973, vol. 31, pp. 55-64.
(Continued)

*Primary Examiner* — In Suk Bullock
*Assistant Examiner* — Aaron Pierpont
(74) *Attorney, Agent, or Firm* — Howard V. Owens

(57) ABSTRACT

The present invention relates to a new process which comprises the steps of hydrotreating, paraffin disproportionation and hydroisomerization to convert biological hydrocarbonaceous oxygenated oils comprising triglycerides into biologically-derived paraffinic jet/diesel fuels, solvents and base oils. A combination of conventional hydrogenation/dehydrogenation catalysts, such as $Pt/Al_2O_3$, and conventional olefin metathesis catalysts, such as $WO_3/SiO_2$, or inexpensive variations thereof, is generally employed in the paraffin disproportionation step.

19 Claims, 8 Drawing Sheets

(51) Int. Cl.
| | |
|---|---|
| C07C 6/08 | (2006.01) |
| C07C 5/03 | (2006.01) |
| C10L 1/08 | (2006.01) |
| C10L 1/04 | (2006.01) |
| C07C 5/333 | (2006.01) |
| C07C 6/04 | (2006.01) |
| C10G 3/00 | (2006.01) |
| B01J 23/652 | (2006.01) |
| C07C 5/27 | (2006.01) |
| B01J 35/00 | (2006.01) |
| B01J 23/30 | (2006.01) |
| B01J 23/58 | (2006.01) |
| B01J 37/02 | (2006.01) |

(52) U.S. Cl.
CPC ............... *C07C 5/03* (2013.01); *C07C 5/2775* (2013.01); *C07C 5/333* (2013.01); *C07C 6/00* (2013.01); *C07C 6/02* (2013.01); *C07C 6/08* (2013.01); *C10G 3/42* (2013.01); *C10G 3/44* (2013.01); *C10G 3/47* (2013.01); *C10G 3/48* (2013.01); *C10G 3/50* (2013.01); *C10L 1/04* (2013.01); *C10L 1/08* (2013.01); *B01J 23/30* (2013.01); *B01J 23/58* (2013.01); *B01J 35/0006* (2013.01); *B01J 37/0201* (2013.01); *C07C 2523/652* (2013.01); *C07C 2529/85* (2013.01); *C10G 2300/1011* (2013.01); *C10G 2300/1014* (2013.01); *C10G 2300/1018* (2013.01); *C10G 2400/02* (2013.01); *C10G 2400/04* (2013.01); *C10G 2400/08* (2013.01); *C10G 2400/10* (2013.01); *C10L 2200/0469* (2013.01); *C10L 2270/026* (2013.01); *C10L 2270/04* (2013.01); *Y02P 30/20* (2015.11)

(56) References Cited

U.S. PATENT DOCUMENTS

| | | | |
|---|---|---|---|
| 3,718,576 | A | 2/1973 | Hughes et al. |
| 3,728,410 | A | 4/1973 | Hughes |
| 3,773,845 | A | 11/1973 | Hughes |
| 3,775,505 | A * | 11/1973 | Hughes ............. 585/708 |
| 3,784,622 | A | 1/1974 | Hughes |
| 3,793,251 | A | 2/1974 | Hughes |
| 3,808,285 | A | 4/1974 | Hughes |
| 3,856,876 | A | 12/1974 | Burnett |
| 3,864,417 | A | 2/1975 | Hughes |
| 3,914,330 | A | 10/1975 | Hughes |
| 5,565,088 | A * | 10/1996 | Nair et al. ............. 208/58 |
| 6,225,359 | B1 | 5/2001 | O'Rear et al. |
| 6,441,263 | B1 * | 8/2002 | O'Rear et al. ......... 585/650 |
| 6,562,230 | B1 | 5/2003 | O'Rear et al. |
| 6,566,568 | B1 | 5/2003 | Chen |
| 6,573,416 | B1 * | 6/2003 | Randolph ............. 585/708 |
| 6,632,765 | B1 | 10/2003 | Chen |
| 2002/0111521 | A1* | 8/2002 | O'Rear ............ C10G 2/32 585/326 |
| 2011/0071327 | A1* | 3/2011 | Abhari et al. ......... 585/240 |

OTHER PUBLICATIONS

C. Y. Chen et al., "Disproportionation of Alkanes via Molecular Redistribution and Molecular Averaging", Collect. Czech. Chem. Commun., 2008, vol. 73, Nos. 8-9, pp. 1105-1111.

* cited by examiner

PARAFFINIC JET AND DIESEL FUELS AND BASE OILS FROM VEGETABLE OILS VIA A COMBINATION OF HYDROTREATING, PARAFFIN DISPROPORTIONATION AND HYDROISOMERIZATION

RELATED APPLICATIONS

The present application is a continuation of U.S. application Ser. No. 13/841,226 filed Mar. 15, 2013, which claims the benefit of Provisional Patent Application No. 61/754,375 filed on Jan. 18, 2013, the disclosures of both of which are herein incorporated by reference in their entireties.

BACKGROUND OF THE INVENTION

Biological products are in demand to replace those made from petroleum and other non-renewable resources. Biological resources, however, have very different compositions and properties in comparison to petroleum. Novel methods of making the products in demand from biological resources are therefore required.

Triglycerides from vegetable oils such as soybean oil and canola oil are a particular type of biological resource and one type of biological hydrocarbonaceous oxygenated oil. These can be either fats or oils. They are composed of a glycerol backbone esterified with three fatty acids. The fatty acids can be either saturated or unsaturated. The fatty acids typically contain straight hydrocarbonaceous chains with between 6 and 24 carbon atoms per molecule. Each biological resource provides triglycerides composed of fatty acids with chains containing only a few narrowly defined numbers of carbon atoms. When these fatty acids are converted into paraffins, the distribution of the resulting paraffins is often narrow in terms of the length of the molecular chains (i.e., the carbon atom number per molecule), and inconsistent with the intended product use, e.g., for jet and diesel fuels, solvents and base oils.

Biological triglycerides can be hydrogenated to form paraffins, and these paraffins typically fall in the boiling range of diesel or jet fuel. In this aspect, U.S. Patent Application Publication No 2004/0230085 teaches a process for saturation of triglycerides, but employs an isomerization catalyst. The product contains 73 wt % iso-paraffins and only 13% n-paraffins. This process also does not describe how to make lighter paraffins useful as biologically-derived paraffinic solvents, or how to make heavier paraffins useful as biologically-derived paraffinic base oils.

Molecular Redistribution is a technique of paraffin disproportionation that can redistribute a paraffin feed into its lighter and heavier analogues with a broader boiling range centered at the same average molecular weight. Such a process is disclosed in U.S. Pat. No. 6,566,569, which employs a feedstock composed predominantly of pentanes. The entire disclosure is incorporated by reference in this application. There is no teaching in the patent, however, of the use of triglycerides as a feedstock. Furthermore, there has been no teaching of the production of biologically-derived paraffinic jet and diesel fuels, biologically-derived paraffinic solvents or biologically-derived paraffinic base oils.

SUMMARY OF THE INVENTION

A process for preparing a paraffin product stream from feed comprising triglycerides is disclosed. The process involves contacting a triglyceride feedstock with a catalyst that includes a hydrotreating catalyst under conditions which hydrogenate the fatty acids of the triglycerides to long chain paraffins having a narrow boiling range, followed by contacting the resulting paraffins with a paraffin disproportionation catalyst to broaden the boiling range of the paraffin products. The paraffin disproportionation catalysts such as Molecular Redistribution catalysts have a hydrogenation/dehydrogenation component as well as an olefin metathesis component, for creation of lighter and heavier analogues of the feed paraffins. In the paraffin disproportionation reactions, the feed paraffins are first dehydrogenated to their corresponding olefins over the hydrogenation/dehydrogenation component of the catalyst. These olefins are then metathesized to their lighter and heavier analogues over the olefin metathesis component of the catalyst. The resulting olefins are then hydrogenated to their corresponding paraffins. This process provides a paraffin product stream which may possess carbon chains in the range from 2 through approximately 40 carbon atoms.

In one embodiment, the present invention provides a process for the manufacture of biologically-derived paraffinic jet and diesel fuels, solvents and base oils from a biological hydrocarbonaceous oxygenated oil, comprising triglycerides, comprising: (a) hydrotreating the biological hydrocarbonaceous oxygenated oil to form a first effluent mixture comprising propane, carbon monoxide, carbon dioxide, water and a n-paraffinic product; (b) recovering the n-paraffinic product from the first effluent mixture; and (c) converting the n-paraffinic product of step (b) over a paraffin disproportionation catalyst to form a second effluent mixture comprising a light n-paraffinic biologically derived product and a heavy n-paraffinic biologically derived product.

DETAILED DESCRIPTION OF THE INVENTION

Figure 1A:
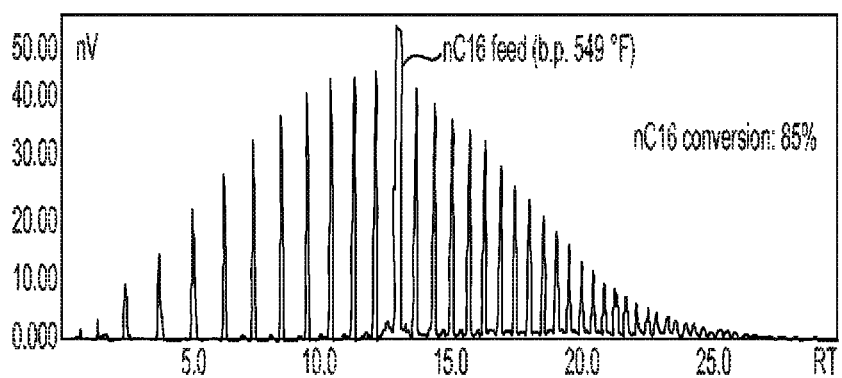
FIG. 1A is gas chromatographic data of the products produced via Molecular Redistribution of n-hexadecane (Example 4) at 650° F., 1000 psig and 0.5 LHSV.

In some embodiments, the present invention provides a process for the manufacture of biologically-derived paraffinic jet and diesel fuels, solvents and base oils from a biological hydrocarbonaceous oxygenated oil, further comprising: (d) recovering the light n-paraffinic biologically derived product from step (c); and (e) recovering the heavy n-paraffinic biologically derived product from step (c).

In some embodiments, the present invention provides a process for the manufacture of biologically-derived paraffinic jet and diesel fuels, solvents and base oils from a biological hydrocarbonaceous oxygenated oil, further comprising an isomerization step of the n-paraffinic product from step (b).

In some embodiments, the present invention provides a process for the manufacture of biologically-derived paraffinic jet and diesel fuels, solvents and base oils from a biological hydrocarbonaceous oxygenated oil, further comprising an isomerization step of the second effluent mixture from step (c).

In some embodiments, the present invention provides a process for the manufacture of biologically-derived paraffinic jet and diesel fuels, solvents and base oils from a biological hydrocarbonaceous oxygenated oil, further comprising an isomerization step of the light n-paraffinic biologically derived product, heavy n-paraffinic biologically derived product, or both the light and heavy paraffinic biologically derived products.

In some embodiments, the present invention provides the triglyceride is a mixture of triglycerides.

In some embodiments, the present invention provides the biological hydrocarbonaceous oxygenated oil is selected from the group consisting of rapeseed oil, colza oil, canola oil, tall oil, sunflower oil, soybean oil, hempseed oil, olive oil, linseed oil, mustard oil, palm oil, peanut oil, castor oil, coconut oil, lard, tallow and train oil.

In some embodiments, the present invention provides a process for the manufacture of biologically-derived paraffinic jet and diesel fuels, solvents and base oils from a biological hydrocarbonaceous oxygenated oil, wherein step (c) further comprises: treatment of the n-paraffinic product of step (b) with a hydrogenation/dehydrogenation catalyst and an olefin metathesis catalyst under conditions which dehydrogenate the paraffins to olefins, metathesize the olefins, and hydrogenate the olefins to paraffins to provide the second effluent mixture comprising a light n-paraffinic biologically derived product and a heavy n-paraffinic biologically derived product.

In some embodiments, the present invention provides a hydrogenation/dehydrogenation catalyst includes at least one metal or a corresponding metal compound selected from the group consisting of iron, cobalt, nickel, ruthenium, rhodium, palladium, osmium, iridium and platinum.

In some embodiments, the present invention provides a hydrogenation/dehydrogenation catalyst comprises a metal or corresponding metal compound selected from the group consisting of rhenium, tin, germanium, gallium, indium, lead, tin and mixtures thereof.

In some embodiments, the present invention provides an olefin metathesis catalyst comprises a metal or corresponding metal compound is selected from the group consisting of tungsten, molybdenum, tin and rhenium.

In some embodiments, the present invention provides an olefin metathesis catalyst comprises tungsten.

In some embodiments, the present invention provides a hydrogenation/dehydrogenation catalyst comprises platinum or a platinum compound and the olefin metathesis catalyst comprises tungsten.

In some embodiments, the present invention provides a hydrogenation/dehydrogenation catalyst is platinum-on-alumina and the olefin metathesis catalyst is tungsten-on-silica and the volumetric ratio of the platinum component to the tungsten component is greater than 1:50 and less than 50:1, and wherein the amount of platinum on the alumina is within the range of from about 0.01 weight percent to about 10 weight percent on an elemental basis and the amount of tungsten on the silica is within the range of from about 0.01 weight percent to about 50 weight percent on an elemental basis.

In some embodiments, the present invention provides a volumetric ratio of the platinum component to the tungsten component is between 1:10 and 10:1 and wherein the amount of platinum on the alumina is within the range of from about 0.1 weight percent to about 5.0 weight percent on an elemental basis and the amount of tungsten on the silica is within the range of from about 0.1 weight percent to about 20 weight percent on an elemental basis.

In some embodiments, the present invention provides that step (c) further comprises a temperature between about 400° F. to 1000° F.

In some embodiments, the present invention provides that step (c) further comprises a pressure between about 50 psig to 3000 psig.

In some embodiments, the present invention provides that step (c) further comprises a liquid hourly space velocity between about 0.1 to 5 $h^{-1}$.

In some embodiments, the present invention provides that step (a) further comprises a temperature for hydrotreating between about 300° F. to 750° F.

In some embodiments, the present invention provides that step (a) further comprises a total reaction pressure for hydrotreating between about 50 to 3000 psig.

In some embodiments, the present invention provides that step (a) further comprises a liquid hourly space velocity for hydrotreating between about 0.1 to 5 $h^{-1}$.

In some embodiments, the present invention provides that step (a) further comprises a hydrogen feed rate for hydrotreating between about 0.1 to 20 MSCF/bbl.

In some embodiments, the present invention provides a temperature for the isomerization between about 200° F. to 900° F.

In some embodiments, the present invention provides total reaction pressure for the isomerization between about 15 to 3000 psig.

In some embodiments, the present invention provides a liquid hourly space velocity for the isomerization between about 0.1 and about 5 $h^{-1}$.

In some embodiments, the present invention provides a hydrogen feed rate for the isomerization between about 0.1 to 30 MSCF/bbl.

In some embodiments, the present invention provides a biological hydrocarbonaceous oxygenated oil will not include appreciable amounts (i.e., amounts that would adversely affect the catalyst used for paraffin disproportionation) of hydrogen, alkenes, alkynes, thiols, amines, water, air, oxygenates or cycloparaffins.

In some embodiments, the present invention provides an n-paraffinic product comprising at least 90 wt % n-paraffins.

In its broadest aspect, the present invention is directed to an integrated process for producing paraffinic product streams varying in molecular chain length from a feedstock that includes triglycerides. The process involves obtaining an appropriate triglyceride feedstock, hydrotreating the triglycerides to form n-paraffins, dehydrogenating the n-paraffins to create olefins, metathesizing the resulting olefins, and hydrogenating the resulting metathesized olefins to form paraffins which are the lighter and heavier analogues of the starting n-paraffins. The dehydrogenation, metathesis and hydrogenation steps preferably occur in the same reactor. All steps also preferably occur in the same reactor. The process described herein is an integrated process. As used herein the term "integrated process" refers to a process which involves a sequence of steps, some of which may be parallel to other steps in the process, but which are interrelated or somehow dependent upon either earlier or later steps in the total process.

An advantage of the present process is the effectiveness and relatively inexpensive processing costs with which the present process may be used to prepare high quality components for incorporation into jet fuel and diesel compositions. In particular, an advantage is that feedstocks that are not conventionally recognized as suitable sources for such product streams can be used.

Feedstocks for the Hydrotreating Reaction

As the feedstock, a biological raw material containing fatty acids and/or fatty acid esters that originate from plants, animals or fish is used, said biomaterial being selected from the group consisting of vegetable oils and fats, animal fats, fish oils and mixtures thereof. Examples of suitable biomaterials are wood-based and other plant-based fats and oils such as rapeseed oil, colza oil, canola oil, tall oil, sunflower oil, soybean oil, hempseed oil, olive oil, linseed oil, mustard oil, palm oil, peanut oil, castor oil, coconut oil, as well as fats contained in plants bred by means of gene manipulation, animal-based fats such as lard, tallow, train oil, and fats contained in milk as well as recycled fats of the food industry and mixtures of the above.

The basic structural unit of a typical vegetable or animal fat useful as the feedstock is a triglyceride. Specifically, the triglyceride is a triester of glycerol with three fatty acid molecules, having the structure presented in the following formula I:

"Triglyceride" refers to class of molecules having the general formula (1):

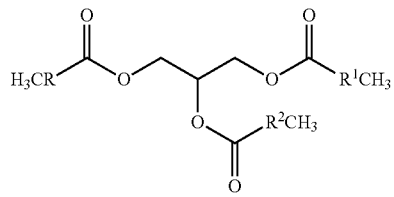

wherein R, $R^1$ and $R^2$ are independently aliphatic residues having from 6 to 24 carbon atoms (e.g., from 8 to 20 carbon atoms, or from 10 to 16 carbon atoms). The term "aliphatic" means a straight (i.e., un-branched) or branched, substituted or un-substituted hydrocarbon chain that is completely saturated or that contains one or more unsaturated carbon-carbon bonds. The fatty acid composition may vary considerably in feedstocks of different origin.

Hydrotreating Chemistry and Catalysts

The term "hydrotreating" is given its conventional meaning and describes processes that are well known to those skilled in the art. Hydrotreating refers to a catalytic process, usually carried out in the presence of free hydrogen, in which the primary purpose is the desulfurization, denitrification and/or deoxygenation of the feedstock. Generally, in hydrotreating operations, cracking of the hydrocarbon molecules, i.e., breaking the larger hydrocarbon molecules into smaller hydrocarbon molecules is minimized and the unsaturated hydrocarbons are either fully or partially hydrogenated.

Catalysts used in carrying out hydrotreating operations are well known in the art. See, for example, see U.S. Pat. Nos. 4,347,121 and 4,810,357 for general descriptions of hydrotreating, and some typical catalysts used in hydrotreating processes. The hydrotreating catalyst can be a "supported catalyst" which refers to a catalyst in which the active components, e.g., Group VIII and Group VIB metals or compounds thereof, are deposited on a carrier or support. Alternatively, it can be a "self-supported catalyst". "Self-supported catalyst" can be used interchangeably with "unsupported catalyst," or "bulk catalyst," meaning that the catalyst composition is NOT of the conventional catalyst form which has a preformed, shaped catalyst support which is then loaded with metal compounds via impregnation or deposition. In one embodiment, the self-supported catalyst is formed through precipitation. In another embodiment, the self-supported catalyst has a binder incorporated into the catalyst composition. In yet another embodiment, the self-supported catalyst is formed from metal compounds and without any binder.

"Catalyst precursor" in one embodiment refers to a compound containing at least a metal selected from Group IIA, Group IIB, Group IVA, Group VIII metals and combinations thereof (e.g., one or more Group IIA metals, one or more Group IIB metals, one or more Group IVA metals, one or more Group VIII metals, and combinations thereof); at least a Group VIB metal; and, optionally, one or more organic oxygen-containing promoters, and which compound can be used directly in the upgrade of a renewable feedstock (as a catalyst), or can be sulfided for use as a sulfided hydroprocessing catalyst.

"Group IIA" or "Group IIA metal" refers to beryllium (Be), magnesium (Mg), calcium (Ca), strontium (Sr), barium (Ba), radium (Ra), and combinations thereof in any of elemental, compound, or ionic form.

"Group IIB" or "Group IIB metal" refers to zinc (Zn), cadmium (Cd), mercury (Hg), and combinations thereof in any of elemental, compound, or ionic form.

"Group IVA" or "Group IVA metal" refers to germanium (Ge), tin (Sn) or lead (Pb), and combinations thereof in any of elemental, compound, or ionic form.

"Group VIB" or "Group VIB metal" refers to chromium (Cr), molybdenum (Mo), tungsten (W), and combinations thereof in any of elemental, compound, or ionic form.

"Group VIII" or "Group VIII metal" refers to iron (Fe), cobalt (Co), nickel (Ni), ruthenium (Ru), rhodium (Ro), palladium (Pd), osmium (Os), iridium (Ir), platinum (Pt), and combinations thereof in any of elemental, compound, or ionic form.

The Periodic Table of the Elements refers to the version published by the CRC Press in the *CRC Handbook of Chemistry and Physics*, 88th Edition (2007-2008). The names for families of the elements in the Periodic Table are given here in the Chemical Abstracts Service (CAS) notation.

"Noble metal" refers to a metal selected from ruthenium, rhodium, palladium, silver, osmium, iridium, platinum, and gold.

"Promoter" refers to an organic agent that interacts strongly with inorganic agents (either chemically or physically) in a reaction to form a catalyst or a catalyst precursor, leading to alterations in the structure, surface morphology and composition, which in turn results in enhanced catalytic activity.

"Presulfiding" or "presulfided" refers to the sulfidation of a catalyst precursor in the presence of a sulfiding agent such as $H_2S$ or dimethyl disulfide (DMDS) under sulfiding conditions, prior to contact with a feedstock in an upgrade process.

Promoted Catalyst—Self-Supported Catalyst:

In one embodiment, the catalyst for the upgrade of renewable feedstock is a promoted self-supported catalyst derived from a catalyst precursor. The catalyst precursor can be a hydroxide or oxide material, prepared from at least a Group VIB metal precursor feed and at least another metal precursor feed. The at least another metal precursor can be used interchangeably with $M^P$, referring to a material that enhances the activity of a catalyst (as compared to a catalyst without the at least another metal, e.g., a catalyst with just a Group VIB metal), with the promoter being present in an amount of at least 0.05 to about 5 molar times of the total number of moles of the metals of Group VIB and at least another metal present, e.g., a Group VIII metal. In one embodiment, the promoter is present in an amount of up to 1000 molar times the total number of moles of the metals.

The self-supported or unsupported catalyst precursor made can be converted into a hydroconversion catalyst (becoming catalytically active) upon sulfidation. However, the self-supported catalyst precursor can be used in the conversion of the renewable feedstock by itself (as a catalyst), or it can be sulfided prior to use, or sulfided in-situ in the presence of sulfiding agents in the reactor. In one embodiment, the self-supported catalyst precursor is used unsulfided, with or without any addition of sulfiding agents (e.g., $H_2S$) to the reactor system or inherent in the feed, even for the hydroconversion of a feedstock consisting essentially of renewable materials (without any sulfur present in the feed as sulfiding agent). In one embodiment, a self-supported multi-metallic oxide may also be used. The self-supported multi-metallic oxide comprises at least one Group VIII metal and at least two Group VIB metals. In one embodiment, the ratio of Group VIB metal to Group VIII metal in the precursor ranges from about 10:1 to about 1:10. In another embodiment, the oxide catalyst precursor is represented by the formula: $(X)_b(Mo)_c(W)_dO_f$, wherein X is Ni or Co, Mo is molybdenum, W is tungsten, the molar ratio of b:(c+d) is 0.5:1 to 3:1 (e.g., 0.75:1 to 1.5:1, or 0.75:1 to 1.25:1), the molar ratio of c:d is >0.01:1 (e.g., greater than 0.1:1, 1:10 to 10:1, or 1:3 to 3:1), and f=[2b+6 (c+d)]/2. The oxide catalyst precursor further comprises one or more promoters L. In one embodiment, the self-supported catalyst precursor is of the formula $(NiL)_x(Mo_yW_{1-y})O_{(x+3)}$; wherein L refers to one or more promoters; and wherein x:(1−y) is 1.7-2.4; and y is 0.25 to 0.67. The oxide precursor is generated by combining the Group VIB and group VIII metals, forming a product, then subsequently calcining the product formed thereof.

In another embodiment, the catalyst precursor is in the form of a hydroxide compound, comprising at least one Group VIII metal and at least two Group VIB metals. In one embodiment, the hydroxide catalyst precursor is represented by the formula: $A_v[(M^P)(OH)_x(L)^n_y]_z(M^{VIB}O_4)$, wherein A is one or more monovalent cationic species; $M^P$ has an oxidation state (P) of either +2 or +4 depending on the metal(s) being employed; L is one or more oxygen-containing promoters, and L has a neutral or negative charge n≤0; $M^{VIB}$ is at least a Group VIB metal having an oxidation state of +6; $M^P:M^{VIB}$ has an atomic ratio between 100:1 and 1:100; $v-2+P*z-x*z+n*y*z=0$; and $0 < v \le 2$; $0 < x \le P$; $0 < y \le -P/n$; $0 < z$. In one embodiment, the catalyst precursor is charge-neutral, carrying no net positive or negative charge.

In one embodiment, A is selected from the group consisting of an alkali metal cation, an ammonium cation, an organic ammonium cation and a phosphonium cation.

In one embodiment, $M^P$ has an oxidation state of either +2 or +4. $M^P$ is at least one of a Group IIA metal, Group IIB metal, Group IVA metal, Group VIII metal and combinations thereof. In one embodiment, $M^P$ is at least a Group VIII metal with $M^P$ having an oxidation state P of +2. In another embodiment, $M^P$ is selected from Group IIB metals, Group IVA metals and combinations thereof. In one embodiment, $M^P$ is selected from the group of Group IIB and Group VIA metals such as zinc, cadmium, mercury, germanium, tin or lead, and combinations thereof, in their elemental, compound, or ionic form. In another embodiment, $M^P$ is a Group IIA metal compound, selected from the group of magnesium, calcium, strontium and barium compounds. $M^P$ can be in solution or in partly in the solid state, e.g., a water-insoluble compound such as a carbonate, hydroxide, fumarate, phosphate, phosphite, sulfide, molybdate, tungstate, oxide, or mixtures thereof.

In one embodiment, the promoter L has a neutral or negative charge n≤0. Examples of promoters L include but are not limited to carboxylates, carboxylic acids, aldehydes, ketones, the enolate forms of aldehydes, the enolate forms of ketones, and hemiacetals; organic acid addition salts such as formic acid, acetic acid, propionic acid, maleic acid, malic acid, cluconic acid, fumaric acid, succinic acid, tartaric acid, citric acid, oxalic acid, glyoxylic acid, aspartic acid, alkane sulfonic acids such as methanesulfonic acid and ethanesulfonic acid, aryl sulfonic acids such as benzenesulfonic acid and p-toluenesulfonic acid and arylcarboxylic acids; carboxylate containing compounds such as maleate, formate, acetate, propionate, butyrate, pentanoate, hexanoate, dicarboxylate, and combinations thereof.

In one embodiment, $M^{VIB}$ is at least a Group VIB metal having an oxidation state of +6. In another embodiment, $M^{VIB}$ is a mixture of at least two Group VIB metals, e.g., molybdenum and tungsten. $M^{VIB}$ can be in solution or in partly in the solid state. In one embodiment, $M^P : M^{VIB}$ has a mole ratio of 10:1 to 1:10.

In one embodiment, the self-supported catalyst is prepared from a mixed metal sulfide ("MMS") catalyst precursor, characterized by having an optimized Ni:Mo:W composition with a molar ratio of Ni/W of $1.62 \leq Ni/W \leq 2.5$, a molar ratio of W/Mo is in the range of $0.5 \leq W/Mo \leq 6.0$, and a molar ratio of Ni/(Mo+W) in the range of $0.57 < Ni/(Mo+W) < 2.1$. In another embodiment, the MMS catalyst precursor comprises nickel, molybdenum and tungsten having relative proportions within a compositional range defined by four points ABCD in a ternary phase diagram, with molar fractions of the four points ABCD defined by $A(Ni_x=0.36, Mo_x=0.41, W_x=0.22)$; $B(Ni_y=0.45, Mo_y=0.36, W_y=0.18)$; $C(Ni_z=0.58, Mo_z=0.06, W_z=0.36)$, and $D(Ni_w=0.68, Mo_w=0.05, W_w=0.27)$. The MMS catalyst precursor can be used for the upgrade of the renewable feedstock directly with or without being pre-sulfided, or with or without any sulfiding agents being present or added to the feedstock. Further details regarding the description of the catalyst precursor and the self-supported catalyst formed thereof are described in a number of patents and patent applications, including U.S. Pat. Nos. 6,156,695; 6,162,350; 6,274,530; 6,299,760; 6,566,296; 6,620,313; 6,635,599; 6,652,738; 6,758,963; 6,783,663; 6,860,987; 7,179,366; 7,229,548; 7,232,515; 7,288,182; 7,544,285, 7,615,196; 7,803,735; 7,807,599; 7,816,298; 7,838,696; 7,910,761; 7,931,799; 7,964,524; 7,964,525; 7,964,526; 8,058,203; and U.S. Patent Application Publication Nos. 2007/0090024, 2009/0107886, 2009/0107883, 2009/0107889 and 2009/0111683, the relevant disclosures are included herein by reference.

Embodiments of the process for making the self-supported catalyst precursor are as described in the references indicated above, and incorporated herein by reference. In one embodiment, the first step is a mixing step wherein at least one Group VIB metal precursor feed and at least one another metal precursor feed are combined together in a precipitation step (also called co-gelation or co-precipitation), wherein a catalyst precursor is formed as a gel. The precipitation (or "co-gelation") is carried out at a temperature and pH under which the Group VIB metal compound and at least another metal compound precipitate (e.g., forming a gel). In one embodiment, the temperature is from 25° C. to 350° C. and the pressure is from 0 to 3000 psig (0 to 20.7 MPa gauge). The pH of the reaction mixture can be changed to increase or decrease the rate of precipitation (co-gelation), depending on the desired characteristics of the catalyst precursor product, e.g., an acidic catalyst precursor. In one embodiment, the mixture is left at its natural pH during the reaction step(s). The pH is maintained in the range from 3-9 in one embodiment; and from 5-8 in a second embodiment.

Promoted Catalyst—Supported Catalyst:

In another embodiment, the hydrotreating catalyst is selected from supported catalysts suitable for hydroconversion of renewable feedstocks. Such catalysts comprise at least one metal component selected from Group VIII metals and/or at least one metal component selected from the Group VIB metals. Group VIII metals include iron (Fe), cobalt (Co) and nickel (Ni). Noble metals, such as palladium (Pd) and/or platinum (Pt), can be included in the hydrotreating catalyst. Group VIB metals include chromium (Cr), molybdenum (Mo) and tungsten (W). Group VIII metals can present in the catalyst in an amount of from 0.5 to 25 wt. % (e.g., from 2 to 20 wt. %, 3 to 10 wt. %, 5 to 10 wt. %, or 5 to 8 wt. %) and Group VIB metals can be present in the catalyst in an amount of from 0.5 to 25 wt. % (e.g., from 5 to 20 wt. %, or 10 to 15 wt. %), calculated as metal oxide(s) per 100 parts by weight of total catalyst, where the percentages by weight are based on the weight of the catalyst before sulfiding. The total weight percent of metals employed in the hydrotreating catalyst is at least 5 wt. % in one embodiment. The remainder of the catalyst can be composed of the support material, although optionally other components may be present (e.g., filler, molecular sieve, or the like, or a combination thereof).

The metal components in the supported catalyst can be in the oxide and/or the sulfide form. If a combination of at least a Group VIII and a Group VIB metal component is present as (mixed) oxides, it can be subjected to a pre-sulfiding treatment prior to proper use in hydroprocessing. Suitably, the catalyst usually comprises one or more components of Ni and/or Co and one or more components of Mo and/or W. However, the supported catalyst precursor can be used in the conversion of the renewable feedstock by itself (unsulfided and as a catalyst) with or without any addition of sulfiding agents (e.g., $H_2S$) to the reactor system or inherent in the feed, or it can be pre-sulfided prior to use, or sulfided in-situ in the presence of sulfiding agents in the reactor or in the feed.

The supported catalyst can be prepared by blending, or co-mulling, active sources of the aforementioned metals with a binder. Examples of binders include silica, silicon carbide, amorphous and crystalline silica-aluminas, silica-magnesias, aluminophosphates, boria, titania, zirconia, and the like, as well as mixtures and co-gels thereof. Preferred supports include silica, alumina, alumina-silica, and the crystalline silica-aluminas, particularly those materials classified as clays or zeolitic materials. Especially preferred support materials include alumina, silica, and alumina-silica, particularly either alumina or silica. Other components, such as phosphorous, can be added as desired to tailor the catalyst particles for a desired application. These support materials may be either naturally occurring or in the form of gelatinous precipitates or gels including mixtures of silica and metal oxides. Naturally occurring clays which can be composited with the catalyst include those of the montmorillonite and kaolin families. These clays can be used in the raw state as originally mined or initially subjected to calumniation, acid treatment or chemical modification. The blended components can then shaped, such as by extrusion, dried and calcined at temperatures up to 1200° F. (649° C.) to produce the finished catalyst. Alternatively, other methods of preparing the amorphous catalyst include preparing oxide binder particles, such as by extrusion, drying and calcining, followed by depositing the aforementioned metals on the oxide particles, using methods such as impregnation. The supported catalyst, containing the aforementioned metals, can then further dried and calcined prior to use as a hydrotreating catalyst.

The support materials can be of many types including some that have acidic catalytic activity. Ones that have activity include amorphous silica-alumina or may be a zeolitic or non-zeolitic crystalline molecular sieve. Examples of suitable matrix molecular sieves include zeolite Y, zeolite X and the so-called ultrastable zeolite Y and high structural silica:alumina ratio zeolite Y such as that described in U.S. Pat. Nos. 4,401,556, 4,820,402 and 5,059,567. Small crystal size zeolite Y, such as that described in U.S. Pat. No. 5,073,530, can also be used. Non-zeolitic molecular sieves which can be used include, for example, silicoaluminophosphates (SAPO), ferroaluminophosphate, titanium aluminophosphate, and the various ELAPO molecular sieves described in U.S. Pat. No. 4,913,799 and the references cited therein. Details regarding the preparation of various non-zeolite molecular sieves can be found in U.S. Pat. No. 5,114,563 (SAPO); U.S. Pat. No. 4,913,799 and the various references cited in U.S. Pat. No. 4,913,799. Mesoporous molecular sieves can also be used, for example the M41S family of materials (J. Am. Chem. Soc. 1992, 114, 10834-10843), MCM-41 (U.S. Pat. Nos. 5,246,689, 5,198, 203 and 5,334,368), and MCM-48 (Kresge et al., Nature 359 (1992) 710).

In one embodiment, the supported catalyst is a hydroprocessing catalyst prepared as disclosed in US20090298677A1, the relevant disclosures are included herein by reference, by depositing onto a carrier having a water pore volume a composition comprising at least a Group VIB metal and at least a Group VIII metal of the Periodic Table of the Elements, optionally a phosphorus-containing acidic component, and at least a promoter, deposited onto a carrier having a water pore volume, and then calcining the impregnated carrier at a temperature greater than 200° C. and lower than the decomposition temperature of the promoter. The Group VIB metal in one embodiment is selected from molybdenum Mo and tungsten W. The Group VIII metal is selected from cobalt Co and nickel Ni. The promoter is present in an amount of 0.05 to about 5 molar times of the total number of moles of the metals of Group VIB and Group VIII. In one embodiment, the molar ratio of the Group VIII metal to Group VIB metal is about 0.05 to about 0.75.

In one embodiment, the promoter is selected from the group of hydroxycarboxylic acids, ethylene glycol, glycerol, ethanolamine, polyethylene glycol, hydroquinone, ethylenediamine, ethylenediamine-tetraacetic acid, cysteine, alanine, methionine, gluconic acid, pyridine-2,3-dicarboxylic acid, thiophene-2-carboxylic acid, mercaptosuccinic acid, nicotinic acid, lactose, and acetone-1,3-dicarboxylic acid. In another embodiment, the promoter is selected from hydroxycarboxylic acids such as tartaric acid, malic acid, glyceric acid, citric acid and gluconic acid. In yet another embodiment, the promoter is citric acid.

In one embodiment, the supported catalyst has an average pore size of 1 to 10 nm (e.g., from 5 to 10 nm) and a surface area of from 20 to 400 $m^2/g$ (e.g., from 100 to 300 $m^2/g$).

Reactor System:

The hydroprocessing process for the upgrade of the renewable feedstock can be a single-staged or multiple-staged reactor system. In one embodiment, the process utilizes a single-stage system. The reactor system can be of any reactor type. In one embodiment, the feedstock is processed in a fixed bed reactor. In one embodiment, unreacted triglycerides can be recycled to the reactor of the single-staged reactor system (having only one reactor) or to one of the reactors in the multiple-staged reactor system (having multiple reactors) for further processing to maximize production of the desired product(s).

In one embodiment, the reactor system comprises at least two reactors in series with the different reactors employing the same or different catalysts. In another embodiment, the reactor comprises a single reactor having at least two catalyst zones, with the different catalyst zones employing the same or different catalysts. In a third embodiment, the system is a single reactor containing a single catalyst type, a self-supported catalyst or a supported catalyst.

In one embodiment of a reactor system employing different catalysts, the different catalysts are employed in a layered or stacked bed reactor system. By "layered" or "stacked bed," it is meant that the first catalyst appears in a separate catalyst layer, bed, reactor, or reaction zone, and the second catalyst appears in a separate catalyst layer, bed, reactor, or reaction zone downstream, in relation to the flow of the feed, from the first catalyst. In one embodiment of a stacked bed system, the system comprises about 5-95 vol. % of the first catalyst with the second catalyst comprising the remainder. In a second embodiment, the volume ratio of the first catalyst is about 30-60 vol. %. In a third embodiment, the volume ratio of the first catalyst ranges from 5 to about 50 vol. %. In one embodiment of a stacked bed system, the first catalyst is a supported catalyst, and the second catalyst is a self-supported catalyst.

Hydroprocessing Conditions:

The hydroprocessing conditions can be selected so that an overall conversion rate of triglycerides in the feedstock is at least 20 wt. %, (e.g., at least 50 wt. %, 60 wt. %, 70 wt. %, 80 wt. %, 90 wt. %, or 95 wt. %). Suitable hydroprocessing conditions can include a temperature of from 302° F. to 752° F. (150° C. to 400° C.), e.g., from 383° F. to 464° F. (195° C. to 240° C.), 491° F. to 662° F. (255° C. to 350° C.), or from 491° F. to 563° F. (255° C. to 295° C.); a total reaction pressure of from 50 to 3000 psig (0.35 to 20.7 MPa gauge), e.g., from 800 to 2000 psig (5.5 to 13.8 MPa gauge), or from 1600 to 2000 psig (11.0 to 13.8 MPa gauge); a liquid hourly space velocity (LHSV) of from 0.1 to 5 $h^{-1}$, e.g., from 0.5 to 2 $h^{-1}$; and a hydrogen feed rate of from 0.1 to 20 MSCF/bbl (thousand standard cubic feet per barrel), e.g., from 1 to 10 MSCF/bbl. Note that a feed rate of 10 MSCF/bbl is equivalent to 1781 L $H_2$/L feed. In one embodiment, the hydroprocessing conditions include a reaction temperature of at least 446° F. (230° C.) and a reaction pressure from 50 to 3000 psig (0.35 to 20.7 MPa gauge) for the liquid effluent having a normal paraffins concentration of at least 90 wt. %.

Paraffin Disproportionation Chemistry and Catalysts

As used herein, "paraffin disproportionation" is a process in which a single paraffin, a mixture of isomeric paraffins, and/or a mixture of paraffins and/or isoparaffins with a narrow molecular weight range is converted into a mixture that includes lighter and heavier paraffins than those in the starting paraffin or paraffinic mixture. "Molecular Redistribution" is one of these processes.

Molecular Redistribution typically uses a combination of conventional hydrogenation/dehydrogenation catalysts, such as Pt/$Al_2O_3$, and conventional olefin metathesis catalysts, such as $WO_3$/$SiO_2$, or inexpensive variations thereof. The chemistry does not require using hydrogen gas, and therefore does not require relatively expensive recycle gas compressors. The chemistry is typically performed at mild pressures (100-3000 psig). The chemistry is typically thermoneutral and, therefore, there is no need for expensive reactor quench systems or interstage reheaters to control the temperature.

Depending on the nature of the catalysts, Molecular Redistribution catalysts may be sensitive to impurities in the feedstock, such as nitrogen and sulfur-containing compounds and moisture, and these may need to be removed prior to the reaction. The presence of excess olefins and hydrogen in the Molecular Redistribution zone are also known to affect the equilibrium of the Molecular Distribution reaction and may possibly deactivate the catalyst. Since the composition of the fractions may vary, some routine experimentation will be necessary to identify the contaminants that are present and identify the optimal processing scheme and catalyst to use in carrying out the invention.

Molecular Redistribution, as described herein, generally involves two distinct chemical reactions. First, the paraffins are converted into olefins on the hydrogenation/dehydrogenation catalyst in a process known as dehydrogenation or unsaturation. The resulting olefins are molecularly redistributed, or disproportionated, into lighter and heavier olefins by a process known as olefin metathesis upon contacting the metathesis catalyst. The metathesized olefins are then converted into paraffins in a process known as hydrogenation or saturation upon contact with the hydrogenation/dehydrogenation catalyst. For example, a $C_5$ containing feedstock is molecularly redistributed, or disproportionated, to produce a product stream that includes $C_{4-}$ and $C_{6+}$ hydrocarbons.

Various catalysts are known to catalyze the Molecular Redistribution reaction. The catalyst used to carry out the present invention has both hydrogenation/dehydrogenation activity and olefin metathesis activity. The dehydrogenation activity is believed to be necessary to convert the paraffins to olefins, which are believed to be the actual species that undergo olefin metathesis to make olefins lighter and heavier than the starting olefins. Following olefin metathesis, the olefin is converted back into a paraffin. It is theorized that the hydrogenation/dehydrogenation activity of the catalyst also contributes to rehydrogenation of the olefin to a paraffin. While it is not intended that the present invention be limited to any particular mechanism, it may be helpful in explaining the choice of catalysts to further discuss the sequence of chemical reactions which are believed to be responsible for Molecular Redistribution of the paraffins. As an example, the general sequence of reactions for pentane is believed to be:

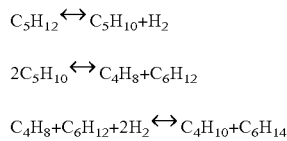

The hydrogenation/dehydrogenation catalyst will typically include a Group VIII metal from the Periodic Table of the Elements, which includes iron, cobalt, nickel, palladium, platinum, rhodium, ruthenium, osmium, and iridium. To minimize the acid-catalyzed reactions such as cracking or coke formation, the acidity of the hydrogenation/dehydrogenation catalyst is often adjusted or eliminated by adding some Group IA or IIA metal cations such as $Li^{+1}$, $Na^{+1}$ or $Mg^{+2}$.

Platinum and palladium or the compounds thereof are preferred for inclusion in the hydrogenation/dehydrogenation component, with platinum or a compound thereof being especially preferred. As noted previously, when referring to a particular metal in this disclosure as being useful in the present invention, the metal may be present as elemental metal or as a compound of the metal. As discussed above, reference to a particular metal in this disclosure is not intended to limit the invention to any particular form of the metal unless the specific name of the compound is given, as in the examples in which specific compounds are named as being used in the preparations.

Usually, the olefin metathesis catalyst will include one or more of a metal or the compound of a metal from Group VIB or Group VIIB of the Periodic Table of the Elements, which include chromium, manganese, molybdenum, rhenium and tungsten. Molybdenum, rhenium, tungsten, and compounds including these metals are preferred for including in the Molecular Redistribution catalyst. Tungsten and compounds including tungsten are particularly preferred. The metals described above may be present as elemental metals or as compounds including the metals, such as, for example, metal oxides. The metals may be present on the catalyst component either alone or in combination with other metals.

In most cases, the metals in the catalyst mass will be supported on a refractory material. Refractory materials suitable for use as a support for the metals include conventional refractory materials used in the manufacture of catalysts for use in the refining industry. Such materials include, but are not necessarily limited to, alumina, zirconia, silica, boria, magnesia, titania and other refractory oxide material or mixtures of two or more of any of the materials. The support may be a naturally occurring material such as clay, or synthetic materials such as silica-alumina and borosilicates. Molecular sieves such as zeolites also have been used as supports for the metals used in carrying out the dual functions of the catalyst mass. See, for example, U.S. Pat. No. 3,668,268. Mesoporous materials such as MCM-41 and MCM-48, such as described in Kresge, C. T., et al., Nature (Vol. 359) pp. 710-712, 1992, may also be used as a refractory support. Other known refractory supports such as carbon may also serve as a support for the active form of the metals in certain embodiments. The support is preferably non-acidic, i.e., having few or no free acid sites on the molecule. Free acid sites on the support may be neutralized by means of alkali metal salts, such as those of lithium. Alumina, particularly alumina on which the acid sites have been neutralized by an alkali salt such as lithium nitrate, is usually preferred as a support for the hydrogenation/dehydrogenation component, and silica is usually preferred as the support for the metathesis component.

The amount of active metal present on the support may vary, but it must be at least a catalytically active amount, i.e., a sufficient amount to catalyze the desired reaction. In the case of the hydrogenation/dehydrogenation component, the active metal content will usually fall within the range from about 0.01 weight percent to about 50 weight percent on an elemental basis, with the range of from about 0.1 weight percent to about 20 weight percent being preferred. For the metathesis component, the active metals content will usually fall within the range of from about 0.01 weight percent to about 50 weight percent on an elemental basis, with the range of from about 0.1 weight percent to about 25 weight percent being preferred.

A typical catalyst for use in the processes described herein includes a platinum component and a tungsten component as described in U.S. Pat. No. 3,856,876, the entire disclosure of which is herein incorporated by reference. In one embodiment of the present invention, the catalyst includes a mixture of platinum-on-alumina and tungsten-on-silica, wherein the volumetric ratio of the platinum component to the tungsten component is greater than 1:50 and less than 50:1. Preferably the volumetric ratio of the platinum component to the tungsten component in this particular embodiment is between 1:10 and 10:1. In one embodiment, both the hydrogenation/dehydrogenation component and the olefin metathesis component are present within the catalyst mass on the same support particle as, for example, a catalyst in which the hydrogenation/dehydrogenation component is dispersed on an unsupported olefin metathesis component such as tungsten oxide. However, in an alternative embodiment, the catalyst components are separated on different particles.

In a reactor having a layered fixed catalyst bed, the two components may, in such an embodiment, be separated in different layers within the bed. However, separate reactors may be used for carrying out the dehydrogenation and olefin metathesis steps. In processing schemes where the dehydrogenation of the paraffins to olefins occurs separately from the olefin metathesis reaction, it may be necessary to include an additional hydrogenation step in the process, since the rehydrogenation of the olefins must take place after the olefin metathesis step.

The process conditions selected for carrying out the present invention will depend upon the Molecular Redistribution catalysts used. In general, the temperature in the reaction zone will be within the range of from about 400° F. (200° C.) to about 1000° F. (540° C.) with temperatures in the range of from about 500° F. (260° C.) to about 850° F. (455° C.) usually being preferred. The pressure in the reaction zone should be maintained above 100 psig, and preferably the pressure should be maintained above 500 psig. The maximum practical pressure for the practice of the invention is about 3000 psig. The feedstock to the Molecular Redistribution preferably should contain no added hydrogen.

In the event the catalyst deactivates with the time-on-stream, specific processes that are well known to those skilled in art are available for the regeneration of the catalysts.

Different reactor types can be used, such as fixed bed, fluidized bed, ebullated bed, etc. An example of a suitable reactor is a catalytic distillation reactor which would permit continuous recovery of the desired lower and higher molecular weight products. Fractional distillation may be employed in order to separate products.

Isomerization of the Intermediate and Final Products

It may be desirable to isomerize the intermediate or final paraffin products of this invention, increasing branching, octane value of the gasoline product and/or the low-temperature properties of the heavier products.

Isomerization processes are typically carried out at a temperature of from 200° F. to 900° F. (93° C. to 482° C.), e.g., from 300° F. to 800° F. (149° C. to 427° C.), or from 400° F. to 800° F. (204° C. to 427° C.); a total reaction pressure of from 15 to 3000 psig (0.1 to 20.7 MPa gauge), e.g., from 50 to 2500 psig (0.3 to 17.2 MPa gauge); a LHSV of from 0.1 to 10 $h^{-1}$, e.g., from 0.25 to 5 $h^{-1}$; and a hydrogen gas treat rate of from 0.1 to 30 MSCF/bbl, e.g., from 0.2 to 20 MSCF/bbl, or from 0.4 to 10 MSCF/bbl. Catalysts useful for isomerization processes are generally bifunctional catalysts that include a hydrogenation component (preferably selected from the Group VIII metals of the Periodic Table of the Elements, and more preferably selected from the group consisting of nickel, platinum, palladium and mixtures thereof) and an acid component. Examples of an acid component useful in the preferred isomerization catalyst include a crystalline zeolite, a halogenated alumina component, or a silica-alumina component. Such paraffin isomerization catalysts are well known in the art.

In some embodiments, the step of isomerizing is carried out using an isomerization catalyst. Suitable such isomerization catalysts can include, but are not limited to, Pt and/or Pd on a support. Suitable supports include, but are not limited to, zeolites CIT-1, IM-5, SSZ-20, SSZ-23, SSZ-24, SSZ-25, SSZ-26, SSZ-31, SSZ-32, SSZ-33, SSZ-35, SSZ-36, SSZ-37, SSZ-41, SSZ-42, SSZ-43, SSZ-44, SSZ-46, SSZ-47, SSZ-48, SSZ-51, SSZ-56, SSZ-57, SSZ-58, SSZ-59, SSZ-60, SSZ-61, SSZ-63, SSZ-64, SSZ-65, SSZ-67, SSZ-68, SSZ-69, SSZ-70, SSZ-71, SSZ-74, SSZ-75, SSZ-76, SSZ-78, SSZ-81, SSZ-82, SSZ-83, SSZ-86, SUZ-4, TNU-9, ZSM-5, ZSM-12, ZSM-22, ZSM-23, ZSM-35, ZSM-48, EMT-type zeolites, FAU-type zeolites, FER-type zeolites, MEL-type zeolites, MFI-type zeolites, MTT-type zeolites, MTW-type zeolites, MWW-type zeolites, TON-type zeolites, other molecular sieves materials based upon crystalline aluminophosphates such as SM-3, SM-7, SAPO-11, SAPO-31, SAPO-41, MAPO-11 and MAPO-31. In some embodiments, the step of isomerizing involves a Pt and/or Pd catalyst supported on an acidic support material selected from the group consisting of beta or zeolite Y molecular sieves, silica, alumina, silica-alumina, and combinations thereof. For other suitable isomerization catalysts, see, e.g., U.S. Pat. Nos. 4,859,312; 5,158,665; and 5,300,210.

With regard to the catalytic isomerization step described above, in some embodiments, the methods described herein can be conducted by contacting the normal paraffins with a fixed stationary bed of catalyst, with a fixed fluidized bed, or with a transport bed. In one embodiment, a trickle-bed operation is employed, wherein such feed is allowed to trickle through a stationary fixed bed, typically in the presence of hydrogen. For an illustration of the operation of such catalysts, see, U.S. Pat. Nos. 6,204,426 and 6,723,889, the relevant disclosures are incorporated herein by reference.

In some embodiments, the isomerized product comprises at least 10 wt. % isoparaffins (e.g., at least 30 wt. %, 50 wt. %, or 70 wt. % isoparaffins). In some embodiments, the isomerized product has an isoparaffin to normal paraffin mole ratio of at least 5:1 (e.g., at least 10:1, 15:1, or 20:1).

In some embodiments, the isomerized product has a boiling range of from 250° F. to 1100° F. (121° C. to 593° C.), e.g., from 280° F. to 572° F. (138° C. to 300° C.), or from 250° F. to 1000° F. (121° C. to 538° C.).

In some embodiments, the isomerized product is suitable (or better suited) for use as a transportation fuel. In some such embodiments, the isomerized product is mixed or admixed with existing transportation fuels in order to create new fuels or to modify the properties of existing fuels. Isomerization and blending can be used to modulate and maintain pour point and cloud point of the fuel or other product at suitable values. In some embodiments, the normal paraffins are blended with other species prior to undergoing catalytic isomerization. In some embodiments, the normal paraffins are blended with the isomerized product.

Other Processes for Altering the Product Stream

In a preferred embodiment, at least a portion of the $C_{6+}$ product stream is reformed, for example using reforming conditions, to form aromatic products. Reforming is a complex process and involves a number of competing processes or reaction sequences. These include dehydrogenation of cyclohexanes to aromatics, dehydroisomerization of alkylcyclopentanes to aromatics, and dehydrocyclization of acyclic hydrocarbons to aromatic. The hydrocracking of paraffins to light products boiling outside the gasoline range and the dealkylation of alkylbenzenes are undesirable reactions in reforming processes. As the $C_{6+}$ product stream includes predominantly acyclic paraffins, the major reforming reaction is dehydrocyclization.

Conditions suitable for reforming $C_{6+}$ product streams are well known in the art. Representative reforming processes include the AROMAX™ process and platforming or rheniforming processes. The AROMAX™ process is well known to those of skill in the art, and is described, for example, in Petroleum & Petrochemical International, Volume 12, No. 12, pages 65 to 68 (1972). Rheniforming processes are also well known to those of skill in the art, and are described, for example, in U.S. Pat. No. 3,415,737, the contents of which are hereby incorporated by reference. The conventional reforming processes all tend to use catalysts that contain Pt and alumina, and frequently contain other elements such as rhenium, iridium, chlorine, fluorine and combinations thereof. Conventional platforming and rheniforming conditions may be preferred for $C_{7+}$ feedstocks, as they provide high yields and the catalysts are relatively stable. The AROMAX™ process is preferred for $C_6$-$C_7$ feedstocks, and tends to give relatively high product yields.

These processes, their commercial startup conditions and their useful range of process operating conditions are all well known to those skilled in the art. These processes can be carried out in a single reactor or in a series of reactors.

Unless otherwise indicated herein, scientific and technical terms used in connection with the present invention shall have the meanings that are commonly understood by those of ordinary skill in the art. Further, unless otherwise required by context, singular terms shall include pluralities and plural terms shall include the singular. More specifically, as used in this specification and the appended claims, the singular forms "a", "an" and "the" include plural referents unless the context clearly dictates otherwise. Thus, for example, reference to "a fatty acid" includes a plurality of fatty acids, and the like. In addition, ranges provided in the specification and appended claims include both end points and all points between the end points. Therefore, a range of 2.0 to 3.0 includes 2.0, 3.0 and all points between 2.0 and 3.0. Furthermore, all numbers expressing quantities, percentages or proportions, and other numerical values used in the specification and claims, are to be understood as being modified in all instances by the term "about". As used herein, the term "include" and its grammatical variants are intended to be non-limiting, such that recitation of items in a list is not to the exclusion of other like items that can be substituted or added to the listed items. As used herein, the term "comprising" means including elements or steps that are identified following that term, but any such elements or steps are not exhaustive, and an embodiment can include other elements or steps.

EXAMPLES

The following illustrative examples are intended to be non-limiting. The following examples will help to further illustrate the invention but are not intended to be a limitation on the scope of the process.

Example 1

Soybean Oil Feed

Soybean oil was purchased from Lucky Supermarket (El Cerrito, Calif.) under the Sunny Select brand. The soybean feed had an API gravity of 21.6 (0.9223 g/mL). The triglycerides of soybean oil are derived mainly from five fatty acids (see, e.g., S. Pinzi et al. Energy & Fuels, 2009, 23, 2325-2341). Table 1 discloses the representative fatty acid composition of soybean oil.

TABLE 1

| Fatty acid | Carbon atoms:Double bonds | Weight Percent |
| --- | --- | --- |
| Palmitic acid | 16:0 | 11 |
| Stearic acid | 18:0 | 4 |
| Oleic acid | 18:1 | 24 |
| Linoleic acid | 18:2 | 54 |
| α-Linoleic acid | 18:3 | 7 |

Example 2

Canola Oil Feed

Canola oil was purchased from the Costco Warehouse (Richmond, Calif.) under the Superb brand. The Canola oil feed had an API gravity of 22.2 (0.9197 g/mL). The triglycerides of Canola oil are derived mainly from five fatty acids according to literature. Table 2 discloses the representative fatty acid composition of Canola oil.

TABLE 2

| Fatty acid | Carbon atoms:Double bonds | Weight Percent |
| --- | --- | --- |
| Palmitic acid | 16:0 | 4 |
| Stearic acid | 18:0 | 2 |
| Oleic acid | 18:1 | 62 |
| Linoleic acid | 18:2 | 22 |
| α-Linoleic acid | 18:3 | 10 |

Example 3

Molecular Redistribution Catalysts

The Molecular Redistribution catalyst employed for paraffin disproportionation in the present invention consisted of a physical mixture of the following two catalysts:
(i) 0.5 wt. % Pt and 0.5 wt. % Li on amorphous $Al_2O_3$ and
(ii) 8.0 wt. % $WO_3$ on amorphous $SiO_2$.

These two catalysts were prepared from the 42-60 mesh particles of $Al_2O_3$ or $SiO_2$ bases as described below:
(1) Preparation of 0.5 wt. % Pt and 0.5 wt. % Li on $Al_2O_3$: 0.3446 grams of $Pt(NH_3)_4(NO_3)_2$ and 1.7263 grams $LiNO_3$ were dissolved in 49.0 grams of water. 34.4 grams of alumina (Condea, 42-60 mesh fraction) were impregnated with this solution at room temperature overnight. The impregnated particles were first dried in a vacuum oven at 250° F. overnight and then calcined in air initially at a temperature of 250° F. for 2 hours, subsequently raised to 700° F. over a period of 5 hours, and finally held at 700° F. for 8 hours. The catalyst was then cooled to room temperature.
(2) Preparation of 8.0 Wt. % $WO_3$ on $SiO_2$:
1.9886 grams of ammonium metatungstate (90.6 wt. % $WO_3$) were dissolved in 48.0 grams of water. 20.72 grams of silica gel manufactured by W.R. Grace/Davison (silica gel grade 59, 42-60 mesh fraction) were impregnated with this solution at room temperature overnight. The resulting impregnated particles were first dried in a vacuum oven at 250° F. overnight and then calcined in the same manner as described above for Pt/Li/$Al_2O_3$ catalyst.

The Molecular Redistribution catalyst was prepared by mixing 2.3 mL of the aforementioned Pt/Li/$Al_2O_3$ catalyst and 1.7 mL of the aforementioned $WO_3$/$SiO_2$ catalyst. The homogenized catalyst mixture (4.0 mL total catalyst volume) had a volume ratio of 5:4 for Pt/Li/$Al_2O_3$ to $WO_3$/$SiO_2$.

In the flow type fixed bed catalytic experiments, the Molecular Redistribution catalyst (4.0 mL of total catalyst volume) prepared above was loaded into a ¼ inch stainless steel tube reactor which was mounted into an electric furnace containing three heating zones. The catalyst mixture was first dried in nitrogen flow (100 mL/min) at atmospheric pressure from room temperature to 400° F. within a period of one hour and held at 400° F. for one hour. The catalyst was then reduced in hydrogen flow (100 mL/min) using a temperature program consisting of 400° F. to 900° F. within one hour and holding it at 900° F. for 12 hours. Subsequently the catalyst was cooled down to 200° F. in the same hydrogen flow and then purged with a nitrogen flow (100 mL/min) for about one hour. The nitrogen purge was necessary to remove the hydrogen present in the reactor system.

The nitrogen was then switched to a feed (e.g., n-hexadecane, paraffins produced from soybean oil or Canola oil via hydrotreating) delivered from an Isco pump. The reactor was subsequently pressurized with the feed at 200° F. from the atmospheric pressure to a preset reaction pressure such as 500 or 1000 psig.

The Molecular Redistribution reaction was then started at a preset pressure (500 or 1000 psig) and a preset LHSV of 0.5 or 1.0 by using a temperature program from 200° F. to a preset temperature (e.g., 650 or 750° F.) at a rate of 2° F./min. During the Molecular Redistribution reactions, no carrier gas such as $H_2$ or $N_2$ was added into the reactor system; only the feed went through the catalyst bed. The liquid Molecular Redistribution product produced at the preset LHSV (0.5 or 1.0), the preset pressure (500 or 1000 psig) and the preset temperature (650 or 750° F.) was collected at room temperature as the effluent after being depressurized from the reactor (500 or 1000 psig) to atmospheric pressure via a Kammer valve which was installed at the reactor exit to maintain the reactor pressure.

The collected liquid Molecular Redistribution product was analyzed with an off-line GC and a GC-based simulated distillation (ASTM D-2887). The effluent was also analyzed with an on-line GC via a six-way sampling valve every 3 hours. Very little amounts of gas products (methane and ethane) were detected.

Example 4

Molecular Redistribution of n-Hexadecane

A Molecular Redistribution reaction experiment with normal hexadecane (n-$C_{16}H_{34}$) as feed was carried out over a Molecular Redistribution catalyst of Example 3 (consisting of Pt/Li/$Al_2O_3$ and $WO_3$/$SiO_2$) at 650° F., 1000 psig and 0.5 LHSV. Both C15– and C17+ normal paraffins were produced. The conversion of n-hexadecane was 85 wt. %. The gas chromatographic results of the product are depicted in FIG. 1A.

Example 5

Molecular Redistribution of n-Eicosane

Figure 1B:
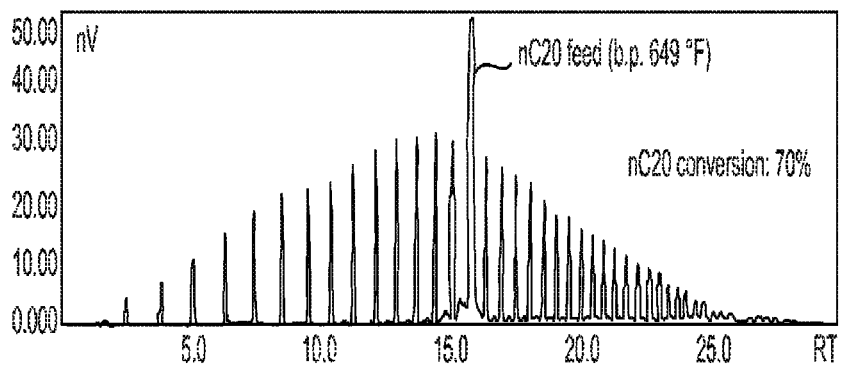
FIG. 1B is gas chromatographic data of the products produced via Molecular Redistribution of n-eicosane (Example 5) at 650° F., 1000 psig and 0.5 LHSV.

A Molecular Redistribution reaction experiment with normal eicosane (n-$C_{20}H_{42}$) as feed was carried out over a Molecular Redistribution catalyst of Example 3 (consisting of Pt/Li/$Al_2O_3$ and $WO_3$/$SiO_2$) at 650° F., 1000 psig and 0.5 LHSV. Both C19– and C21+ normal paraffins were produced. The conversion of n-eicosane was 70 wt. %. The gas chromatographic results of the product are depicted in FIG. 1B.

Example 6

Figure 2A:
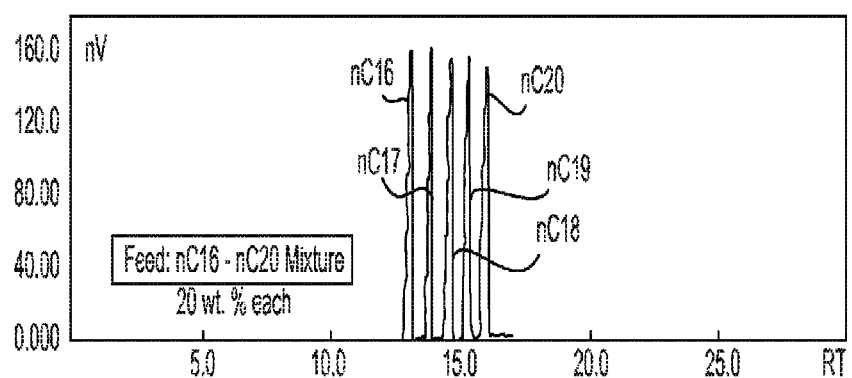
FIGS. 2A and 2B are the gas chromatographic results of the feed and product produced, respectively, via Molecular Redistribution of a mixture of n-hexadecane, n-heptadecane, n-octadecane, n-nonadecane and n-eicosane at 650° F., 1000 psig and 0.5 LHSV (Example 6).
Figure 2:
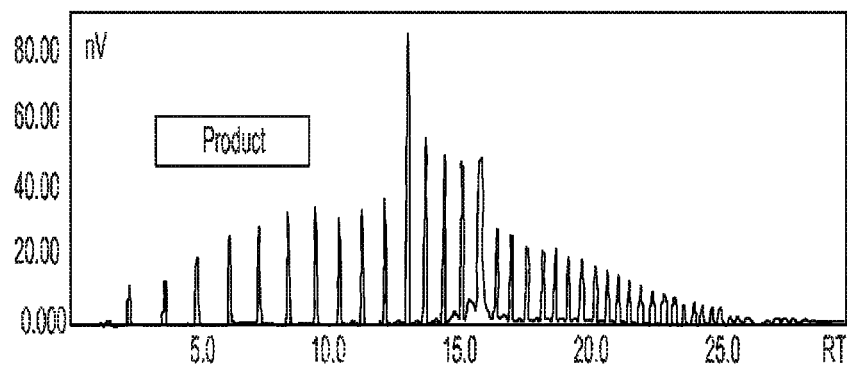

Molecular Redistribution of a Mixture of n-Hexadecane, n-Heptadecane, n-Octadecane, n-Nonadecane and n-Eicosane A mixture was made of n-hexadecane (n-$C_{16}H_{34}$), n-heptadecane (n-$C_{17}H_{36}$), n-octadecane (n-$C_{18}H_{38}$), n-nonadecane (n-$C_{19}H_{40}$) and n-eicosane (n-$C_{20}H_{42}$), with each component in 20 wt. %. A Molecular Redistribution reaction experiment with this mixture as feed was carried out over a Molecular Redistribution catalyst of Example 3 (consisting of Pt/Li/$Al_2O_3$ and $WO_3$/$SiO_2$) at 650° F., 1000 psig and 0.5 LHSV. Both C15– and C21+ normal paraffins were produced. The gas chromatographic results of the feed and product are depicted in FIGS. 2A and 2B, respectively.

Example 7

Molecular Redistribution of n-Hexadecane

Figure 3A:
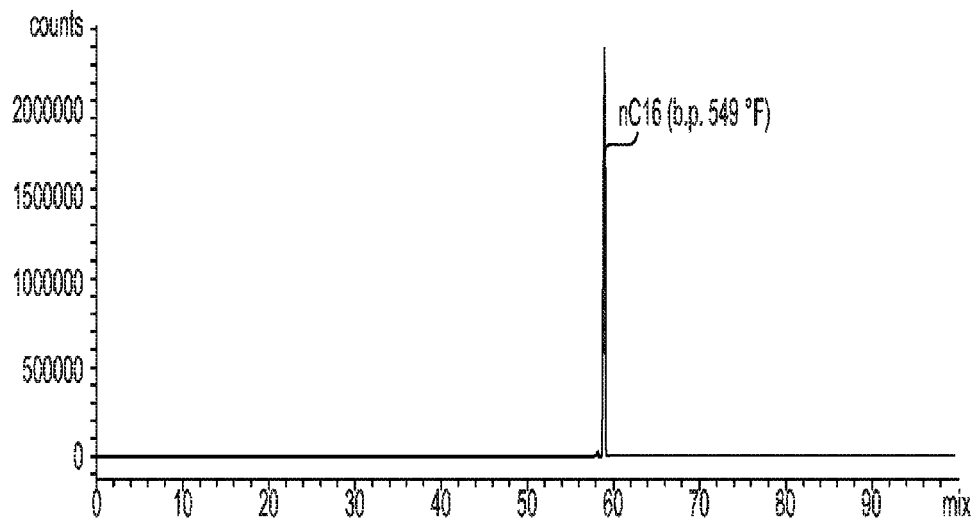
FIGS. 3A and 3B are the gas chromatographic results of the n-hexadecane feed and its Molecular Redistribution product, respectively, via Molecular Redistribution of n-hexadecane at 750° F., 500 psig and 0.5 LHSV (Example 7).
Figure 3B:
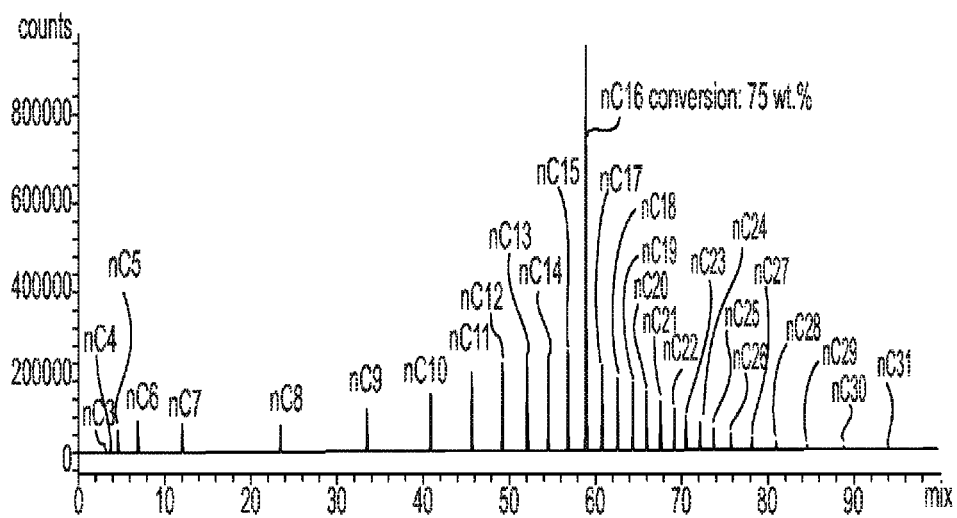
Figure 4:
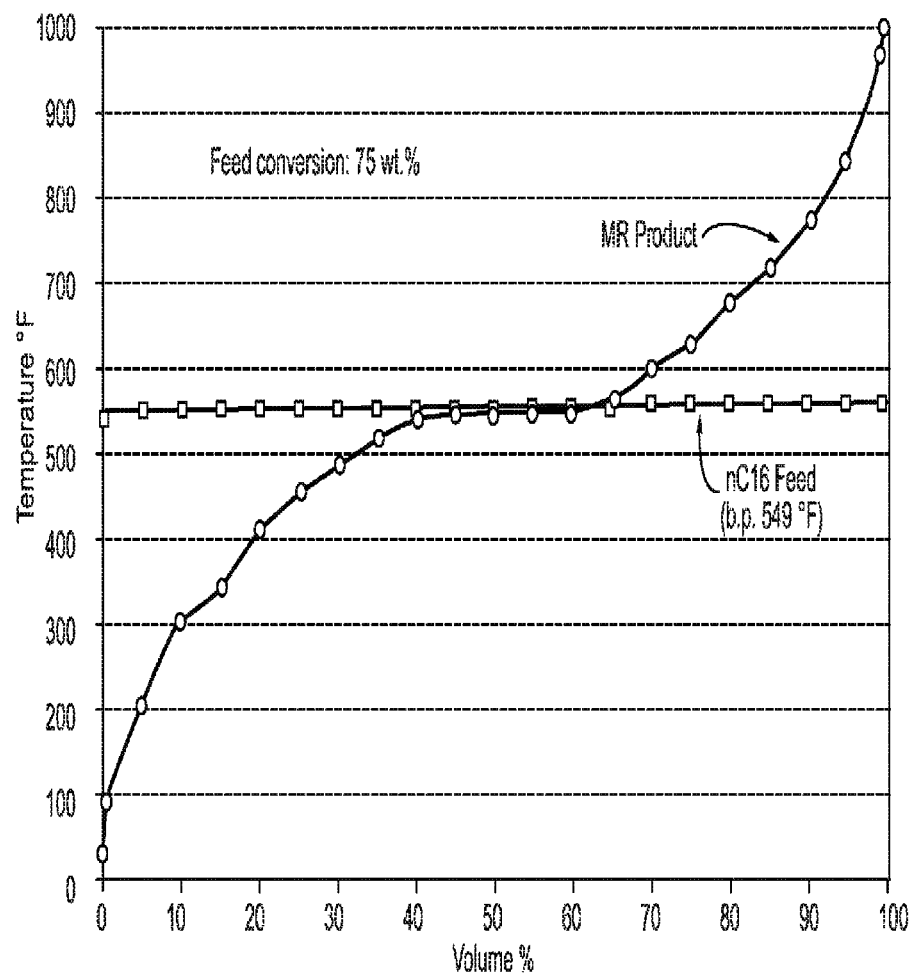
FIG. 4 is the distillation data (boiling point vs. volume %) of the feed and product produced via Molecular Redistribution of n-hexadecane at 750° F., 500 psig and 0.5 LHSV (Example 7), as determined by the simulated distillation (ASTM D-2887 which is based on gas chromatography).

A Molecular Redistribution reaction experiment with normal hexadecane (n-$C_{16}H_{34}$) as feed was carried out over a Molecular Redistribution catalyst of Example 3 (consisting of Pt/Li/$Al_2O_3$ and $WO_3$/$SiO_2$) at 750° F., 500 psig and 0.5 LHSV. Both C15– and C17+ normal paraffins were produced. The conversion of n-hexadecane was 75 wt. %. The gas chromatographic results of the n-hexadecane feed and its Molecular Redistribution product are depicted in FIGS. 3A and 3B, respectively. FIG. 4 shows the distillation data (boiling point vs. volume %) of the n-hexadecane feed and its Molecular Redistribution product of this example, as determined by the simulated distillation (ASTM D-2887 which is based on gas chromatography).

Example 8

Hydrotreating of Soybean Oil

The soybean oil feed from Example 1 was hydrotreated under hydroprocessing conditions in a single reactor over a promoted catalyst based on a Ni—Mo—W-maleate catalyst precursor (prepared as described in Example 1 of U.S. Pat. No. 7,807,599) and sulfided with dimethyl disulfide gas (as described in Example 6 of U.S. Pat. No. 7,807,599). The reactor conditions included a total reaction pressure of 1000 psig, 600° F., a hydrogen gas rate of 8.0 MSCF/bbl, and an LHSV of 1.0 $h^{-1}$.

Figure 5A:
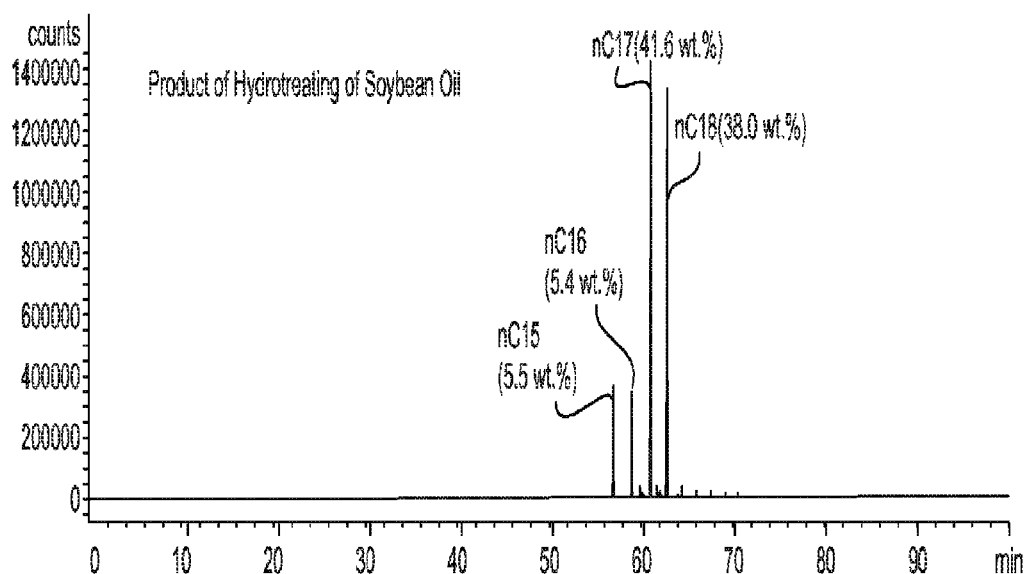
FIG. 5A shows the gas chromatographic data of the hydrotreating product produced from soybean oil in Example 8 at 600° F., 1000 psig, a hydrogen gas rate of 8.0 MSCF/bbl and an LHSV of 1.0 $h^{-1}$.
Figure 6:
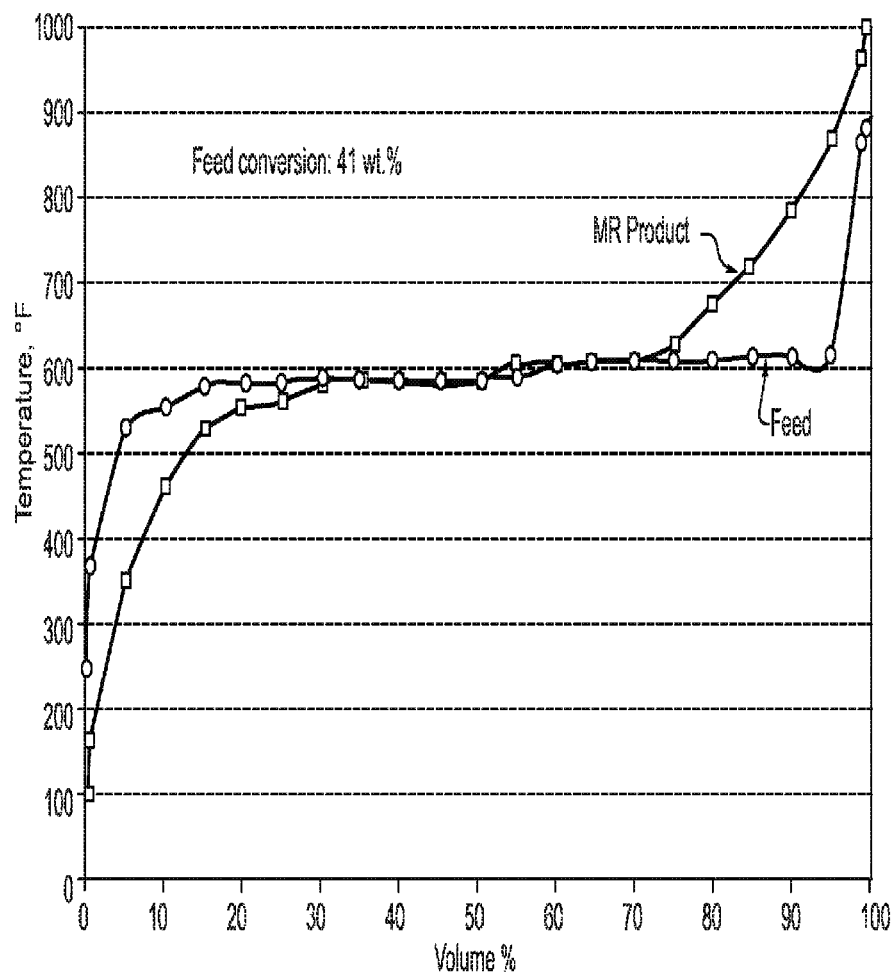
FIG. 6 is the distillation data (boiling point vs. volume %) of (a) the hydrotreating product produced from soybean oil in Example 8 at 600° F., 1000 psig, a hydrogen gas rate of 8.0 MSCF/bbl and an LHSV of 1.0 $h^{-1}$ and (b) the product produced in Example 9 via Molecular Redistribution of the above hydrotreating product of soybean oil at 750° F., 500 psig and 0.5 LHSV, as determined by the simulated distillation (ASTM D-2887 which is based on gas chromatography).

The composition of the liquid product from the hydrotreating of soybean oil was determined by gas chromatography and is reported in FIG. 5A. The major product components were n-pentadecane (n-$C_{15}H_{32}$), n-hexadecane (n-$C_{16}H_{34}$), n-heptadecane (n-$C_{12}H_{36}$) and n-octadecane (n-$C_{18}H_{38}$). The distillation data (boiling point vs. volume %) of the liquid product from the hydrotreating of soybean oil were also acquired via the simulated distillation (ASTM D-2887 which is based on gas chromatography) and are reported in FIG. 6.

Example 9

Molecular Redistribution of the Hydrotreating Product of Soybean Oil

Figure 5B:
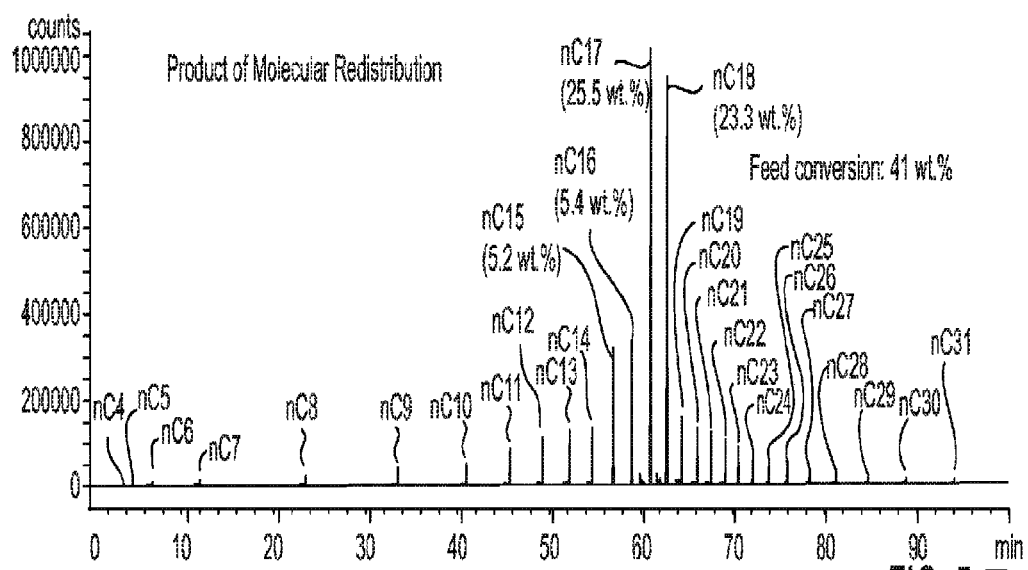
FIG. 5B shows the gas chromatographic data of the product produced in Example 9 via Molecular Redistribution of the above hydrotreating product of soybean oil at 750° F., 500 psig and 0.5 LHSV.

A Molecular Redistribution reaction experiment with the hydrotreating product of soybean oil, produced in Example 8, was carried out over a Molecular Redistribution catalyst of Example 3 (consisting of Pt/Li/$Al_2O_3$ and $WO_3$/$SiO_2$) at 750° F., 500 psig and 0.5 LHSV. The composition of the liquid product from Molecular Redistribution was determined by gas chromatography and is reported in FIG. 5B. Both C14– and C19+ normal paraffins were produced. The conversion of the feed was 41 wt. %. The distillation data (boiling point vs. volume %) of the liquid product from Molecular Redistribution were also acquired via the simulated distillation (ASTM D-2887 which is based on gas chromatography) and are reported in FIG. 6.

Example 10

Hydroprocessing of Canola Oil Via Hydrotreating and Hydroisomerization

The Canola oil feed from Example 2 was hydroprocessed in two stages in two serially connected reactors. The first reactor (at 600° F.) contained a promoted hydroprocessing catalyst prepared as disclosed in US20090298677A1, e.g., an alumina-supported Ni—Mo catalyst available from Chevron Lummus Global, having a median pore size of about 8 nm and specific surface area of about 180 m$^2$/g. The second reactor (at 650° F.) contained a Pt/SOPO-11 based hydroisomerization catalyst prepared as disclosed in Example 3 of U.S. Pat. No. 5,939,349. The reactor conditions included a total reaction pressure of 1000 psig, a hydrogen gas rate of 5.0 MSCF/bbl, and a total LHSV of 0.35 h$^{-1}$.

Figure 7A:
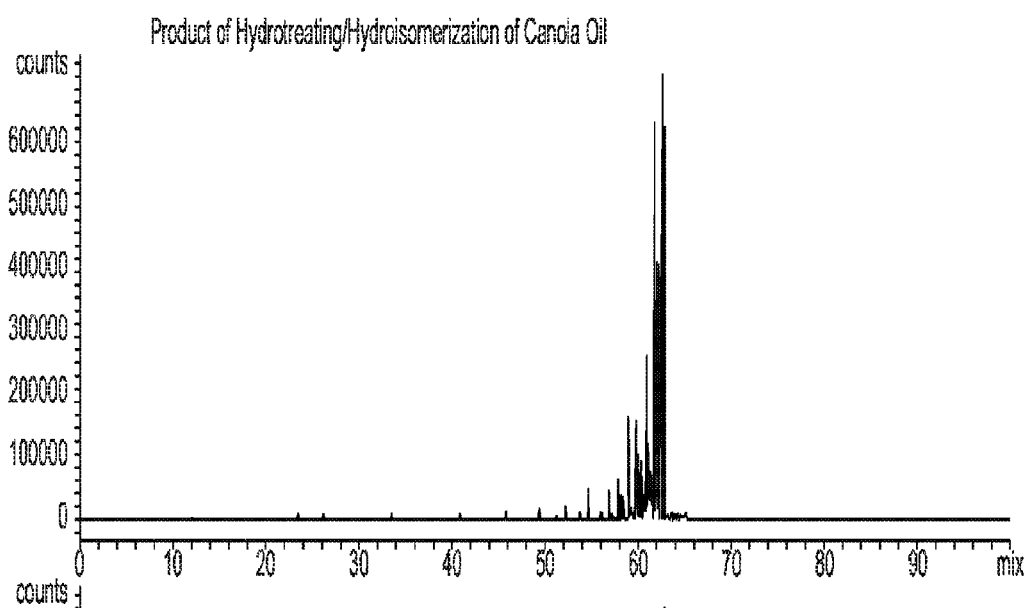
FIG. 7A shows the gas chromatographic data of the hydrotreating-hydroisomerization product produced from Canola oil in Example 10 at 1000 psig, a hydrogen gas rate of 5.0 MSCF/bbl and a total LHSV of 0.35 $h^{-1}$.
Figure 8:
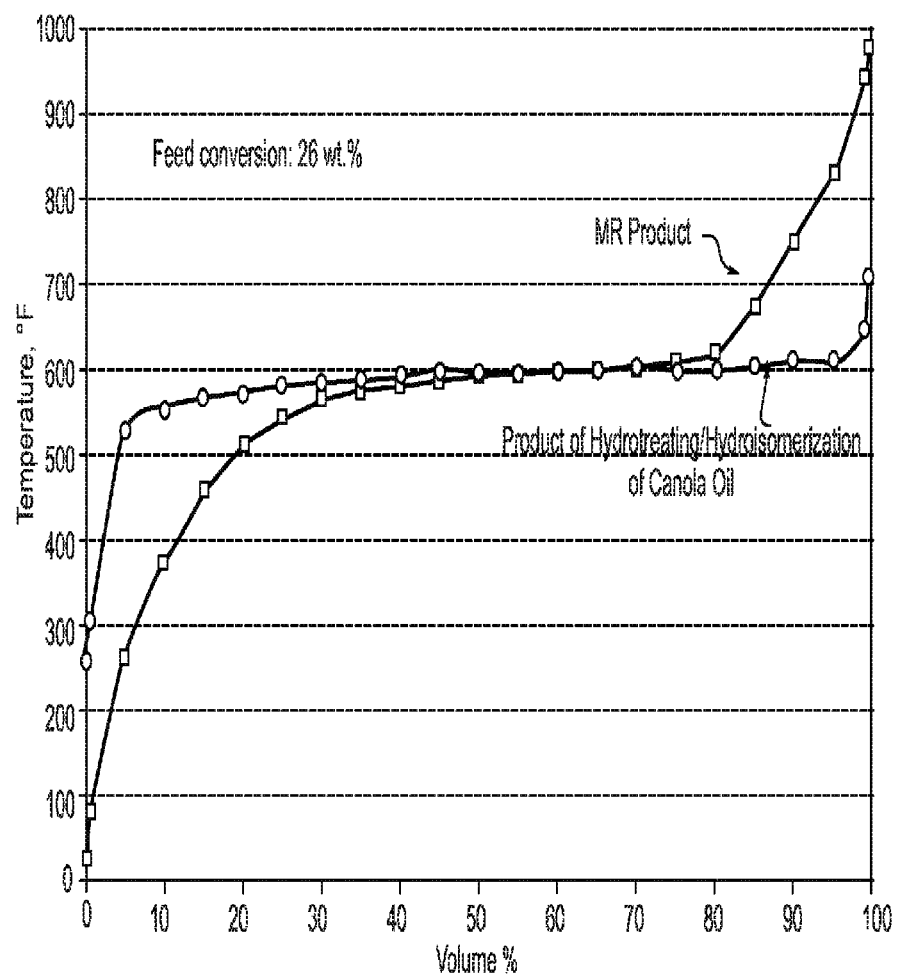
FIG. 8 is the distillation data (boiling point vs. volume %) of (a) the hydrotreating-hydroisomerization product produced from Canola oil in Example 10 at 1000 psig, a hydrogen gas rate of 5.0 MSCF/bbl and a total LHSV of 0.35 $h^{-1}$ and (b) the product produced in Example 11 via Molecular Redistribution of the above hydrotreating-hydroisomerization product of Canola oil at 750° F., 500 psig and 0.5 LHSV, as determined by the simulated distillation (ASTM D-2887 which is based on gas chromatography).

The composition of the liquid product from the hydrotreating and hydroisomerization of Canola oil was determined by gas chromatography and is reported in FIG. 7A. The major product components were iso-octadecanes (i-$C_{18}H_{38}$), iso-heptadecanes (i-$C_{17}H_{36}$) and iso-hexadecanes (i-$C_{16}H_{34}$), showing that the n-paraffins produced via hydrotreating of Canola oil in the first reactor were isomerized via hydroisomerization in the second reactor. The distillation data (boiling point vs. volume %) of the liquid product from the hydrotreating and hydroisomerization of Canola oil were also acquired via the simulated distillation (ASTM D-2887 which is based on gas chromatography) and are reported in FIG. 8.

Example 11

Figure 7B:
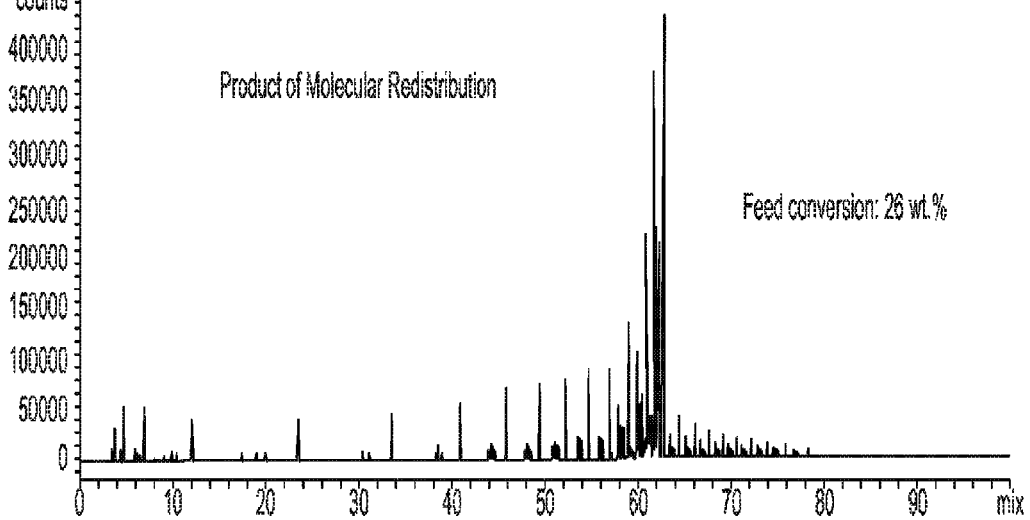
FIG. 7B shows the gas chromatographic data of the product produced in Example 11 via Molecular Redistribution of the hydrotreating-hydroisomerization product of Canola oil at 750° F., 500 psig and 0.5 LHSV.

Molecular Redistribution of the Hydrotreating-Hydroisomerization Product of Canola Oil A Molecular Redistribution reaction experiment with the hydrotreating-hydroisomerization product of Canola oil, produced in Example 10, was carried out over a Molecular Redistribution catalyst of Example 3 (consisting of Pt/Li/Al$_2$O$_3$ and WO$_3$/SiO$_2$) at 750° F., 500 psig and 0.5 LHSV. Both C15− and C19+ paraffins were produced. The composition of the liquid product from Molecular Redistribution was determined by gas chromatography and is reported in FIG. 7B. The conversion of the feed was 26 wt. %. Both lighter and heavier paraffins relative to the feed paraffins were produced. The distillation data (boiling point vs. volume %) of the liquid product from Molecular Redistribution were also acquired via the simulated distillation (ASTM D-2887 which is based on gas chromatography) and are reported in FIG. 8.

All patents, patent applications and publications are herein incorporated by reference to the same extent as if each individual patent, patent application or publication was specifically and individually indicated to be incorporated by reference.

The present invention if not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A process for the manufacture of biologically-derived paraffinic jet and diesel fuels, solvents and base oils from a biological hydrocarbonaceous oxygenated oil comprising triglycerides, the process comprising:
    (a) hydrotreating the biological hydrocarbonaceous oxygenated oil to form a first effluent mixture comprising propane, carbon monoxide, carbon dioxide, water and an n-paraffinic product comprising C16-C20 n-paraffins;
    (b) recovering the n-paraffinic product comprising C16-C20 n-paraffins from the first effluent mixture;
    (c) converting the n-paraffinic product of step (b) over a hydrogenation/dehydrogenation catalyst comprising at least one metal or a corresponding metal compound of palladium or platinum and an olefin metathesis catalyst comprising a metal or corresponding metal compound selected from the group consisting of tungsten, molybdenum, tin and rhenium, under conditions which dehydrogenate the paraffins to olefins, metathesize the olefins, and hydrogenate the olefins to paraffins to form a second effluent mixture comprising (i) a light n-paraffinic biologically derived product comprising C15− jet fuel and (ii) a heavy n-paraffinic biologically derived product comprising C21+ diesel fuel;
    (d) recovering the light n-paraffinic biologically derived product from step (c); and
    (e) recovering the heavy n-paraffinic biologically derived product from step (c).

2. The process of claim 1, further comprising an isomerization step of the n-paraffinic product from step (b).

3. The process of claim 1, further comprising an isomerization step of the second effluent mixture from step (c).

4. The process of claim 1, further comprising an isomerization step of the light n-paraffinic biologically derived product, the heavy n-paraffinic biologically derived product, or both the light and heavy n-paraffinic biologically derived products.

5. The process of claim 1, wherein the triglycerides are a mixture of two or more different triglycerides.

6. The process of claim 1, wherein the biological hydrocarbonaceous oxygenated oil is selected from the group consisting of rapeseed oil, colza oil, canola oil, tall oil, sunflower oil, soybean oil, hempseed oil, olive oil, linseed oil, mustard oil, palm oil, peanut oil, castor oil, coconut oil, lard, tallow, and train oil.

7. The process of claim 1, wherein the hydrogenation/dehydrogenation catalyst further comprises a metal or corresponding metal compound selected from the group consisting of rhenium, tin, germanium, gallium, indium, lead, and mixtures thereof.

8. The process of claim 1, wherein the olefin metathesis catalyst comprises tungsten.

9. The process of claim 1, wherein the hydrogenation/dehydrogenation catalyst comprises platinum or a platinum compound and the olefin metathesis catalyst comprises tungsten.

10. The process of claim 9, wherein the hydrogenation/dehydrogenation catalyst is platinum-on-alumina and the olefin metathesis catalyst is tungsten-on-silica and the volumetric ratio of the platinum component to the tungsten component is greater than 1:50 and less than 50:1, and
    wherein the amount of platinum on the alumina is within the range of from about 0.01 weight percent to about 10 weight percent on an elemental basis and the amount of tungsten on the silica is within the range of from about 0.01 weight percent to about 50 weight percent on an elemental basis.

11. The process of claim 10, wherein the volumetric ratio of the platinum component to the tungsten component is between 1:10 and 10:1 and wherein the amount of platinum on the alumina is within the range of from about 0.1 weight percent to about 5.0 weight percent on an elemental basis and the amount of tungsten on the silica is within the range of from about 0.1 weight percent to about 20 weight percent on an elemental basis.

12. The process of claim 1, wherein step (c) further comprises a temperature between about 400° F. to 1000° F.

13. The process of claim 1, wherein step (c) further comprises a pressure between about 50 psig to 3000 psig.

14. The process of claim 1, wherein step (c) further comprises a liquid hourly space velocity between about 0.1 to 5 $h^{-1}$.

15. The process of claim 1, wherein step (a) further comprises a temperature for hydrotreating between about 300° F. to 750° F.

16. The process of claim 1, wherein step (a) further comprises a total reaction pressure for hydrotreating between about 50 to 3000 psig.

17. The process of claim 1, wherein step (a) further comprises a liquid hourly space velocity for hydrotreating between about 0.1 to 5 $h^{-1}$.

18. The process of claim 1, wherein step (a) further comprises a hydrogen feed rate for hydrotreating between about 0.1 to 20 MSCF/bbl.

19. The process of claim 1, wherein the olefin metathesis catalyst is supported on silica.

* * * * *